(12) United States Patent
Sato et al.

(10) Patent No.: US 8,531,089 B2
(45) Date of Patent: Sep. 10, 2013

(54) ARRAY-TYPE ULTRASONIC VIBRATOR

(75) Inventors: Kazuchika Sato, Kobe (JP); Satoru Hirose, Tondabayashi (JP); Masaki Asano, Nishinomiya (JP)

(73) Assignee: Konica Minolta Medical & Graphic, Inc., Hino-Shi, Tokyo (JP)

( * ) Notice: Subject to any disclaimer, the term of this patent is extended or adjusted under 35 U.S.C. 154(b) by 146 days.

(21) Appl. No.: 13/124,237

(22) PCT Filed: Aug. 21, 2009

(86) PCT No.: PCT/JP2009/064618
§ 371 (c)(1),
(2), (4) Date: Apr. 14, 2011

(87) PCT Pub. No.: WO2010/044312
PCT Pub. Date: Apr. 22, 2010

(65) Prior Publication Data
US 2011/0198968 A1    Aug. 18, 2011

(30) Foreign Application Priority Data

Oct. 17, 2008   (JP) .................................. 2008-268344

(51) Int. Cl.
*H01L 41/08*   (2006.01)
(52) U.S. Cl.
USPC ......................................................... 310/334
(58) Field of Classification Search
USPC .................................................. 310/334–337
See application file for complete search history.

(56) References Cited

U.S. PATENT DOCUMENTS

| | | | | |
|---|---|---|---|---|
| 4,672,591 A | * | 6/1987 | Breimesser et al. | 367/152 |
| 4,701,659 A | * | 10/1987 | Fujii et al. | 310/334 |
| 5,327,895 A | * | 7/1994 | Hashimoto et al. | 600/459 |
| 6,551,248 B2 | | 4/2003 | Miller | |
| 6,666,825 B2 | | 12/2003 | Smith et al. | 600/459 |
| 6,894,425 B1 | * | 5/2005 | Solomon et al. | 310/334 |
| 6,989,625 B2 | * | 1/2006 | Suzuki et al. | 310/334 |
| 7,109,642 B2 | * | 9/2006 | Scott | 310/334 |
| 7,224,104 B2 | * | 5/2007 | Shibamoto et al. | 310/335 |
| 7,696,672 B2 | | 4/2010 | Sugiura et al. | 310/334 |
| 7,794,401 B2 | * | 9/2010 | Kimura et al. | 600/459 |

(Continued)

FOREIGN PATENT DOCUMENTS

| | | |
|---|---|---|
| JP | 03-274899 A | 12/1991 |
| JP | 04-218765 A | 8/1992 |

(Continued)

OTHER PUBLICATIONS

Japanese Notice of Reasons for Rejection dated Sep. 6, 2011, for counterpart Japanese Application No. 2010-089387, together with an English translation thereof.

(Continued)

*Primary Examiner* — Mark Budd
(74) *Attorney, Agent, or Firm* — Buchanan Ingersoll & Rooney PC

(57) ABSTRACT

An array-type ultrasonic vibrator according to the present invention has an acoustic matching layer that has a plate-like body made of a material having a lower acoustic impedance than a plurality of piezoelectric elements. Signal wiring is formed on the plate-like body of the acoustic matching layer. Accordingly, for this array-type ultrasonic vibrator, the signal wiring can be easily formed without using additional components.

12 Claims, 14 Drawing Sheets

(56) References Cited

U.S. PATENT DOCUMENTS

| | | | |
|---|---|---|---|
| 7,919,906 B2 * | 4/2011 | Cerofolini | 310/334 |
| 8,035,278 B2 * | 10/2011 | Shikata et al. | 310/334 |
| 2003/0032884 A1 | 2/2003 | Smith et al. | 600/459 |
| 2006/0184035 A1 | 8/2006 | Kimura et al. | 600/466 |
| 2008/0154135 A1 | 6/2008 | Kimura et al. | 600/463 |
| 2008/0224567 A1 | 9/2008 | Sugiura et al. | 310/322 |

FOREIGN PATENT DOCUMENTS

| | | |
|---|---|---|
| JP | 07-264697 A | 10/1995 |
| JP | 11-155863 A | 6/1999 |
| JP | 2001-268694 A | 9/2001 |
| JP | 2003-125494 A | 4/2003 |
| JP | 2004-208918 A | 7/2004 |
| JP | 2005-507581 A | 3/2005 |
| JP | 2005-229098 A | 8/2005 |
| JP | 2006-166985 A | 6/2006 |
| JP | 2007-513563 A | 5/2007 |
| JP | 2007-172632 A | 7/2007 |
| JP | 2008-187355 A | 8/2008 |
| JP | 2008-244859 A | 10/2008 |
| WO | WO 2005/055195 A1 | 6/2005 |
| WO | WO 2010/044312 A1 | 4/2010 |

OTHER PUBLICATIONS

Japanese Notice of Reasons for Rejection dated Feb. 9, 2010, for counterpart Japanese Application No. 2009-552964, together with an English translation thereof.

Office Action (Decision of Refusal) dated Dec. 6, 2011, issued in the corresponding Japanese Patent Application No. 2010-089387, and an English Translation thereof.

* cited by examiner

ARRAY-TYPE ULTRASONIC VIBRATOR

RELATED APPLICATIONS

This application is a U.S. National Stage Application under 35 U.S.C. 371 of International Application No. PCT/JP2009/064618, filed with the Japanese Patent Office on Aug. 21, 2009.

TECHNICAL FIELD

The present invention relates to array-type ultrasonic vibrators for use in, for example, ultrasonic diagnostic apparatuses and is suitably applied to those having a structure having a two-dimensional array of piezoelectric elements, as well as a laminated structure formed by an organic piezoelectric element and inorganic piezoelectric element.

BACKGROUND ART

Ultrasonic diagnostic apparatuses have been widely used because of their ability to non-invasively obtain tomographic images of a subject such as a living body. In recent years, there have been apparatuses with a two-dimensional array of piezoelectric elements and apparatuses that obtain high-resolution images by using technology called "harmonic imaging." Harmonic imaging generates an image that shows an internal state of a subject, by using, not a frequency (fundamental wave) component of an ultrasonic wave transmitted from an ultrasonic probe into a subject, but a harmonic component, which is extracted from strain components that are generated by the nonlinearlity of the subject when an ultrasonic wave propagates through the subject. As a piezoelectric element that is suitably used in this harmonic imaging, Patent Document 1 proposes an ultrasonic diagnostic apparatus in which a thin organic piezoelectric layer (polyvinylidine difluoride; PVDF) capable of receiving a high-frequency signal of the harmonic component with a high degree of sensitivity is laminated on an inorganic (ceramic) piezoelectric layer (lead zirconium titanate; PZT) capable of high-power transmission. This type of organic-inorganic laminated structure or a structure with a two-dimensional array of piezoelectric elements has an enormous number of signal lines connected to the respective piezoelectric elements. Thus, the layout of the signal lines needs to be devised.

FIG. 14 shows how conventional technology is used for laying out the signal lines in a two-dimensional array of piezoelectric elements. After laminating an individual electrode 2 and a piezoelectric layer 3 on a backing layer 1, the piezoelectric elements are separated into pieces (element isolation). A filler 4 fills the gaps between the piezoelectric elements to flatten the obtained laminated structure, and then a common (GND) electrode 5 and a plurality of acoustic matching layers 6, 7 are laminated thereon. Individual signal lines 8 that are connected respectively to the obtained individual electrodes 2 pass through the backing layer 1 so as to be connected to a wiring substrate, not shown, which is disposed below the backing layer 1.

The backing layer 1 generally attenuates the vibration of the piezoelectric layer 3 that is generated after transmission of the ultrasonic wave, and absorbs the transmitted ultrasonic wave that is emitted rearward, in order to minimize the disturbance of the transmitted ultrasonic wave, which is caused by light reflection, as well as to reduce the pulse width of the transmitted ultrasonic wave. For this reason, the backing layer 1 needs to have a certain thickness. Reducing the pitch of the arrayed piezoelectric elements increases the aspect ratio of through-holes that allow the passage of the signal lines 8, complicating the processing operation. Moreover, finely arranging the elements two-dimensionally increases the output impedance of the piezoelectric elements, causing great transmission loss due to the wiring capacity.

In order to deal with such problems, in Patent Document 2, a thin integrated circuit that is made translucent to ultrasonic waves is interposed between a backing layer and a piezoelectric layer, so that the number of signal lines can be reduced. In addition, the signal lines are pulled out to the side of the array.

Patent Document 3, on the other hand, discloses the use of silicon as the acoustic matching layers.

However, in the technology disclosed in Patent Document 2, an additional integrated circuit board needs to be provided between the backing layer and the piezoelectric layer.

The technology disclosed in Patent Document 3, on the other hand, simply adopts silicon as the material of the acoustic matching layers and uses a side surface of the backing layer to lay out signal lines to be connected to the piezoelectric elements. Therefore, it is difficult to apply the technology disclosed in Patent Document 3 to a device that has, for example, a two-dimensional array of piezoelectric elements or a device that has a laminated structure formed by an organic piezoelectric element and inorganic piezoelectric element.

Patent Document 1: Japanese Patent Application Publication No. 2004-208918
Patent Document 2: Japanese Translation of PCT Application No. 2007-513563
Patent Document 3: Japanese Patent Application Publication No. 2003-125494

SUMMARY OF THE INVENTION

The present invention was contrived in view of the above circumstances, and an object thereof is to provide an array-type ultrasonic vibrator that is capable of simply forming signal wiring without using additional components.

The array-type ultrasonic vibrator according to the present invention has an acoustic matching layer that has a plate-like body made of a material having a lower acoustic impedance than a plurality of piezoelectric elements, wherein signal wiring is formed on the plate-like body of the acoustic matching layer. Therefore, the array-type ultrasonic vibrator of the present invention can simply form the signal wiring without using additional components.

The above and other objects of the present invention as well as the characteristics and advantages thereof will become apparent from a reading of the following description and the accompanying drawings.

BEST MODE FOR CARRYING OUT THE INVENTION

Figure 1:
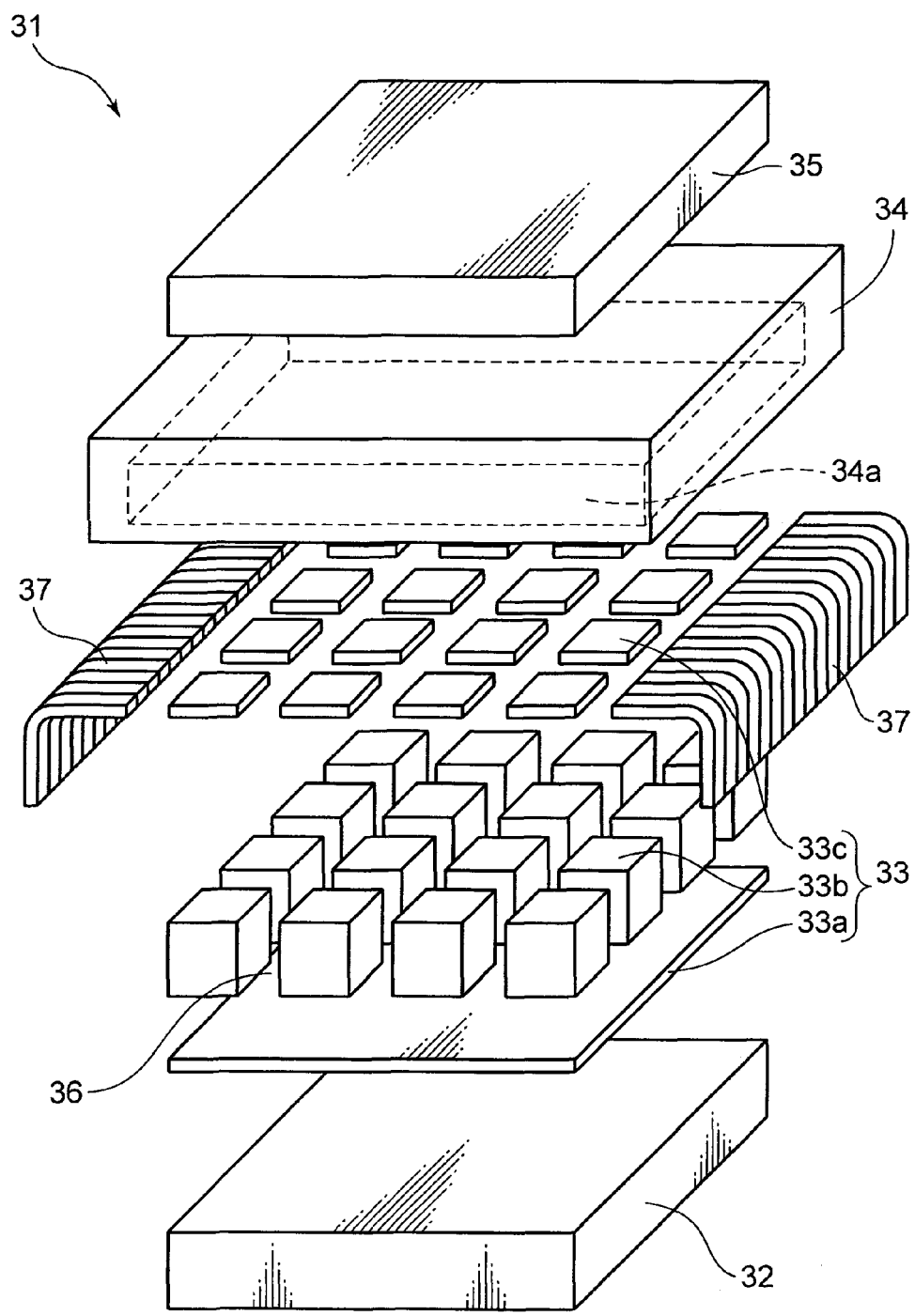
FIG. 1 is an exploded perspective view showing a structural example of an array-type ultrasonic vibrator according to a first embodiment of the present invention.

An embodiment of the present invention is described hereinafter with reference to the drawings. Note that the same reference numerals are used for indicating the same components, and therefore the overlapping explanations are omitted accordingly.

Embodiment 1

Figure 2:
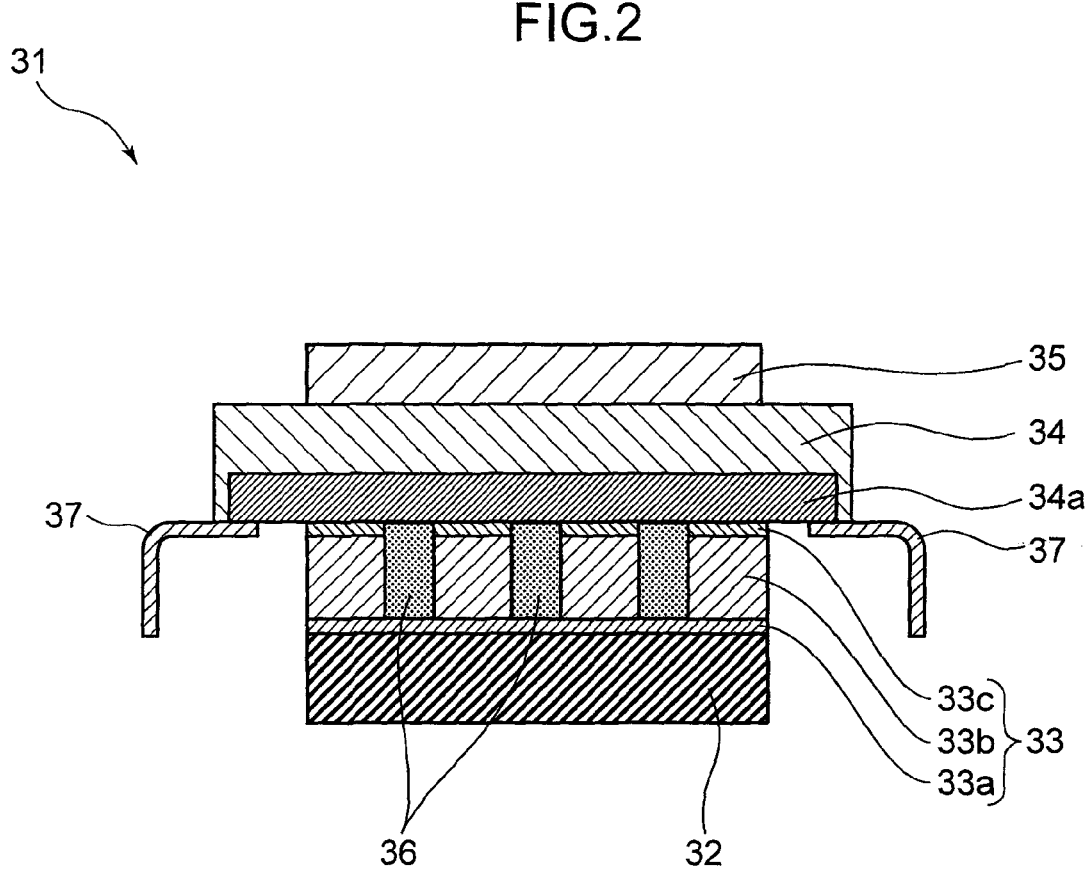
FIG. 2 is a vertical cross-sectional diagram of the array-type ultrasonic vibrator shown in FIG. 1.

FIG. 1 is an exploded perspective view showing a structural example of an array-type ultrasonic vibrator 31 according to a first embodiment of the present invention. FIG. 2 is a vertical cross-sectional diagram of this array-type ultrasonic vibrator. In this array-type ultrasonic vibrator 31, basically two acoustic matching layers 34, 35 are laminated on a backing layer 32, in substantially a sound axis direction, via a plurality of piezoelectric element 33 made of ceramic (e.g., lead zirconium titanate; PZT). The plurality of piezoelectric elements 33, arrayed two-dimensionally in the example shown in FIG. 1, are formed as follows: for example, fixing a piezoelectric layer 33b, also made of the ceramic material mentioned above, onto a supporting substrate, not shown; cutting and isolating thus obtained laminated product into a plurality of elements; filling the gaps between the elements with a filler 36; forming a common (GND) electrode 33a thereon, which is then fixed onto the backing layer 32; peeling the supporting substrate; and laminating an individual electrode 33c. The plurality of piezoelectric element 33 may be produced such that in place of forming the common (GND) electrode 33a in the piezoelectric elements 33, the common (GND) electrode 33a is formed on the backing layer 32 and thus obtained laminated product is bonded onto the piezoelectric layer 33b with an electrically-conductive adhesive.

Figure 3:
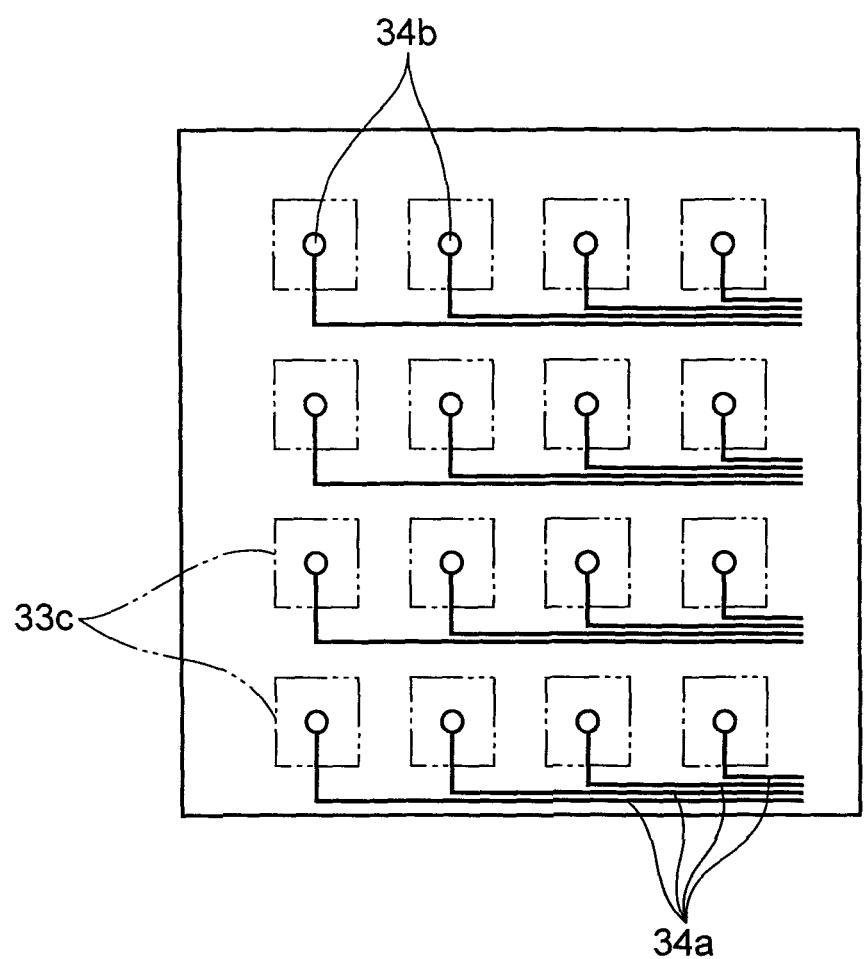
FIG. 3 is a bottom view of an acoustic matching layer of the array-type ultrasonic vibrator shown in FIG. 1.

In the present embodiment, the acoustic matching layer 34 of the piezoelectric elements 33 has a silicon substrate having a lower acoustic impedance than the piezoelectric element 33. Individual signal wiring 34a for each piezoelectric element 33, which is shown in FIG. 3, is formed on the surface of the piezoelectric elements 33. FIG. 3 is a bottom view of the acoustic matching layer 34. As shown in FIG. 2, the individual signal wiring 34a extends horizontally outward (in left and right directions) in the acoustic matching layer 34 and connected to corresponding individual signal wiring formed on a flexible printed substrate 37. The acoustic matching layer 34 has a bump 34b corresponding to the individual electrode 33c, and the sections other then the bump 34b in the individual signal wiring 34a are covered with an insulating coating. It should be noted that the acoustic matching layer 34 may be connected to the flexible printed substrate 37 first and then pasted to the piezoelectric elements 33.

The other acoustic matching layer 35 having a lower acoustic impedance than the acoustic matching layer 34 and higher acoustic impedance than a human body, or a subject, is laminated on the acoustic matching layer 34. This array-type ultrasonic vibrator 31 is connected to, for example, a plurality of cables extending from an integrated circuit, described hereinafter, and then stored in a heated-irradiated housing, to create an ultrasonic probe of the ultrasonic diagnostic apparatus. In the case where the acoustic matching layer 34 alone is used for matching the impedance of the piezoelectric elements 33 with the impedance of the human body, the other acoustic matching layer 35 is not required.

In the array-type ultrasonic vibrator 31 of the present embodiment, the acoustic impedance of the silicon is normally approximately 20 Mrayl. The PZT, on the other hand, has an impedance of approximately 35 Mrayl, and the human body has an impedance of approximately 1.6 Mrayl. Thus, the acoustic matching layer 34 with the silicon substrate can match the acoustic impedance of the piezoelectric elements 33 with the acoustic impedance of the human body. When a frequency of a transmitted ultrasonic wave is, for example, 4 MHz, a wavelength of an ultrasonic wave within the silicon substrate is roughly 2 mm. Accordingly, the thickness of the acoustic matching layer 34 may be set at 0.5 mm equivalent to ¼ of the wavelength. Similarly, the other acoustic matching layer 35 may have an acoustic impedance between the acoustic impedance of the acoustic matching layer 34 and the acoustic impedance of the human body, and a thickness equivalent to ¼ of a wavelength of an ultrasonic wave of the acoustic matching layer 35.

The piezoelectric elements 33 are arrayed at a pitch of, for example, 200 µm, wherein 64×64 elements are arrayed two-dimensionally. In this case, L/S (line width/space) of the individual signal wiring 34a is approximately 3 µm/3 µm, which is wider than the limit of a so-called silicon interposer, 1 µm/1 µm, obtained by forming signal wiring in a silicon substrate. Therefore, the individual signal wiring 34a can be formed on one of the surfaces of the piezoelectric elements 33.

By using a plate-like body bonded to the piezoelectric elements 33 as the acoustic matching layer 34 to form the individual signal wiring 34a for each piezoelectric element 33 on the plate-like body, the individual signal wiring layer 34a can be formed on the backing layer 32, or the individual signal wiring 34a can be formed easily without using additional components, leading to a cost reduction and high definition (increase in the number of elements).

Moreover, the silicon substrate is used as the plate body of the acoustic matching layer 34, so that the individual signal wiring 34a can be formed easily into fine wiring, which is preferred in order to accomplish high definition (increase in the number of elements).

The plate-like body that is bonded to the piezoelectric elements 33 as the acoustic matching layer 34 is not limited to the silicon substrate. It is possible to use a material that is obtained by forming the individual signal wiring 34a onto a glass substrate by means of vapor deposition or transfer, or a flexible printed substrate whose thickness is adjusted appropriately in accordance with an acoustic impedance. For instance, when the plate-like body is made of glass, the acoustic impedance thereof is approximately 12 Mrayl. Even when 32×32 piezoelectric elements 33 are arrayed at a pitch of 500 μm, the L/S (line width/space) of the individual signal wiring 34a is approximately 15 μm/15 μm, which is close to the limit of the flexible printed substrate. When the number of elements increases and the pitch becomes narrow, a multilayer substrate needs to be formed. For this reason, it is preferred to use the silicon substrate in order to achieve high definition (increase in the number of elements). As the piezoelectric layer 33b, on the other hand, $BaTiO_3$ (barium titanate) or the like having an acoustic impedance of approximately 30 Mrayl can be used.

Figure 15:
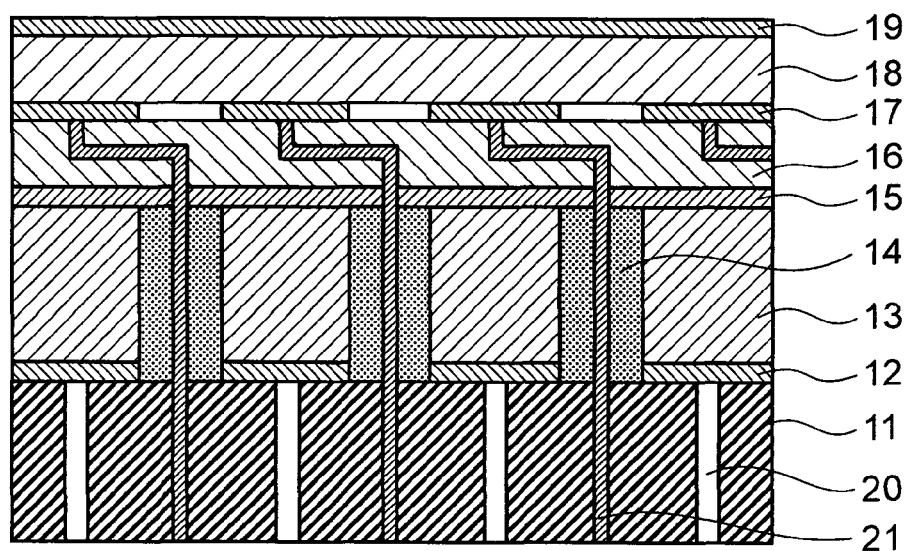
FIG. 15 is a diagram showing a possible way to lay out the signal lines in an array of piezoelectric elements each of which has an organic-inorganic laminated structure.

Next is described a reference example of how signal lines are laid out in an array-type ultrasonic vibrator in which an organic piezoelectric element and inorganic piezoelectric element are laminated. FIG. 15 is a diagram showing the array-type ultrasonic vibrator of this reference example. In FIG. 15, an individual electrode 12 and inorganic piezoelectric layer 13 are laminated on a backing layer 11, and thus obtained laminated product is separated into pieces (element isolation). A filler 14 fills the gaps between the elements to flatten the obtained laminated product, and then a common (GND) electrode 15 is laminated thereon. As a result, an inorganic piezoelectric element is formed. An acoustic matching layer 16 is laminated on this inorganic piezoelectric element, and thereafter individual electrodes 17 are formed in a pattern. An organic piezoelectric layer 18 and common (GND) electrode 19 are laminated thereon to form an organic piezoelectric element. Individual signal lines 20 connected to the separated individual electrodes 12 of the inorganic piezoelectric layer 13 pass through the backing layer 11 so as to be disposed, while individual signal lines 21 connected to the individual electrodes 17 of the organic piezoelectric layer 18 pass through the backing layer 11 from the filler 14 so as to be disposed.

Figure 14:
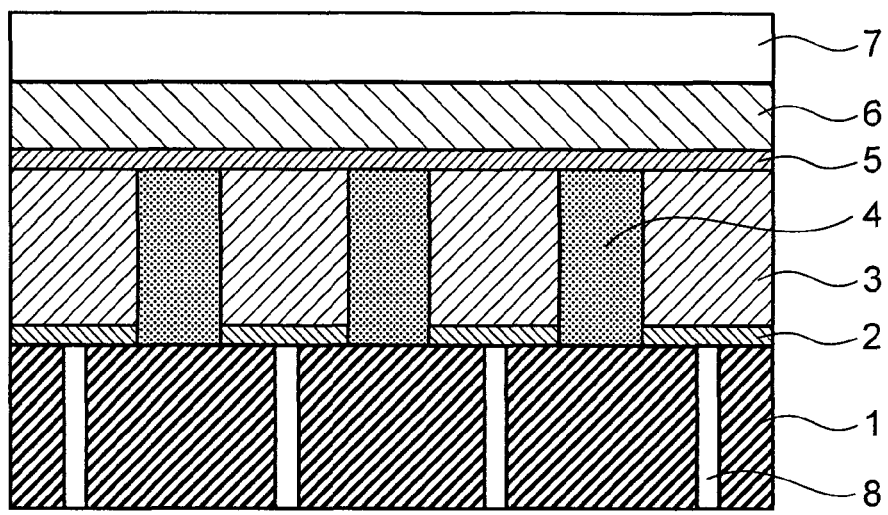
FIG. 14 shows how conventional technology is used for laying out the signal lines in a two-dimensional array of piezoelectric elements.

Therefore, according to the structure of this reference example, in order to lay out the signal lines, the signal lines need to pass through not only the backing layer 11 as described using FIG. 14, but also the filler 14 from the acoustic matching layer 16. This makes it difficult to form wiring of the signal lines in the array-type ultrasonic vibrators having a laminated structure of an organic piezoelectric element and inorganic piezoelectric element.

The following embodiments of the present invention can solve the problems involved in forming signal wiring in the array-type ultrasonic vibrators having a laminated structure of an organic piezoelectric element and inorganic piezoelectric element.

Embodiment 2

Figure 4:
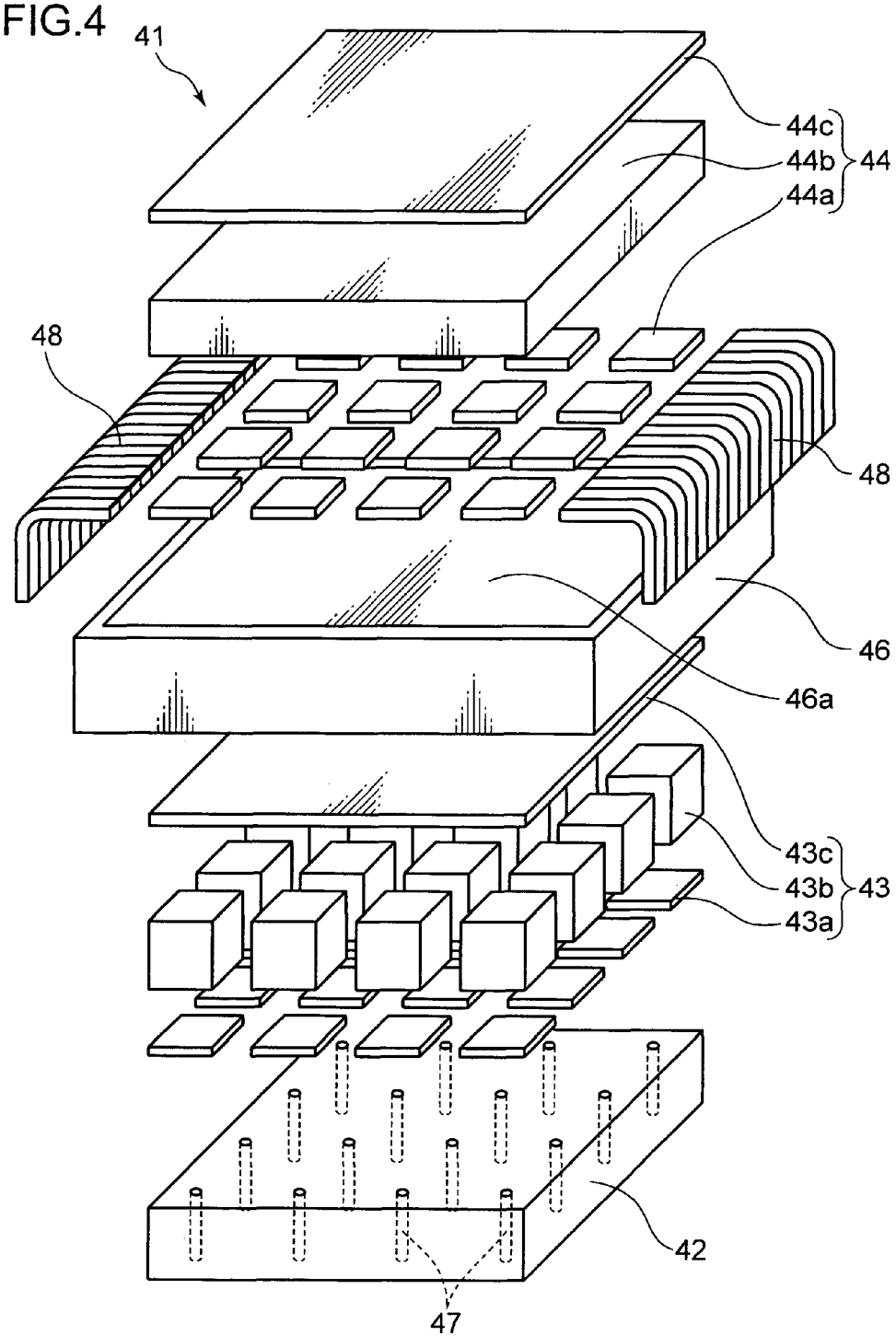
FIG. 4 is an exploded perspective view showing a structural example of an array-type ultrasonic vibrator according to a second embodiment of the present invention.
Figure 5:
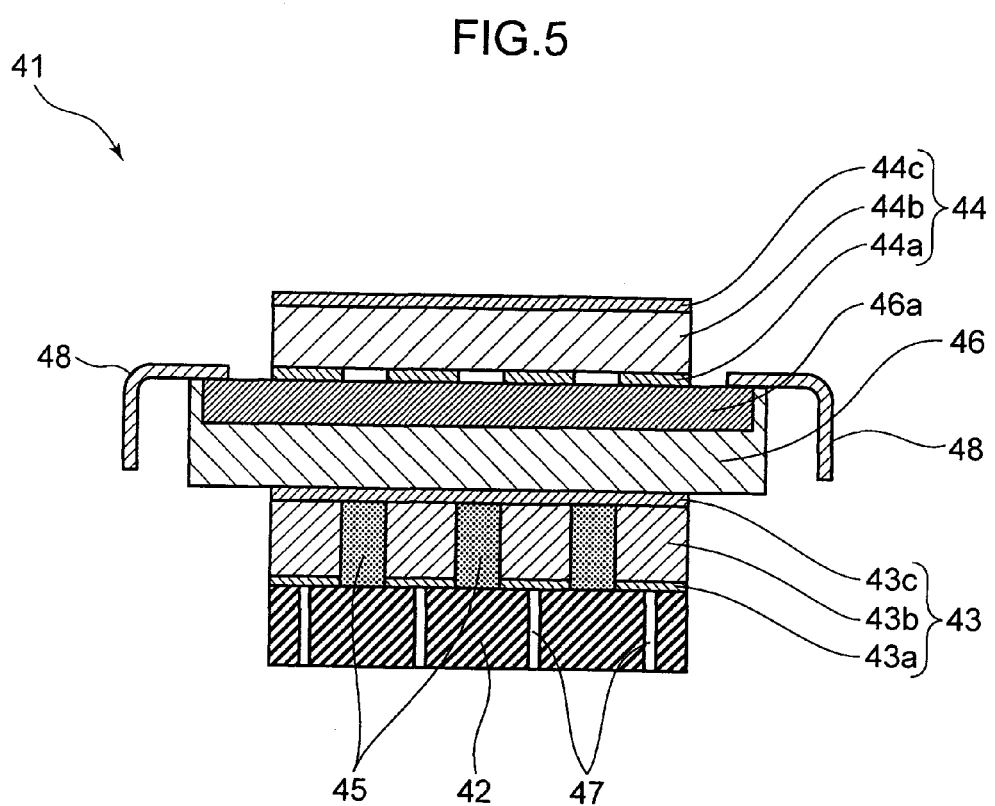
FIG. 5 is a vertical cross-sectional diagram of the array-type ultrasonic vibrator shown in FIG. 4.

FIG. 4 is an exploded perspective view showing a structural example of an array-type ultrasonic vibrator 41 according to a second embodiment of the present invention. FIG. 5 is a vertical cross-sectional diagram of this array-type ultrasonic vibrator. In the array-type ultrasonic vibrator 41, a thin layer of piezoelectric elements 44 made of an organic material (e.g., polyvinylidine difluoride; PVDF), capable of receiving a high-frequency signal with a high degree of sensitivity, and a plurality of inorganic piezoelectric elements 43 made of ceramic (e.g., PZT), capable of high-power transmission, are laminated on a backing layer 42. Harmonic imaging is carried out using a harmonic component received by each organic piezoelectric element 44.

In the inorganic piezoelectric element 43, an individual electrode 43a and a ceramic inorganic piezoelectric layer 43b are laminated on the backing layer 42, and thus obtained laminated structure is separated into pieces (element isolation) so the separated individual electrodes 43a are connected to individual signal wiring 47 passing through the backing layer 42. A filler 45 fills the gaps between the elements to flatten the obtained laminated structure, and a common (GND) electrode 43c is laminated thereon. An acoustic matching layer 46 is then laminated thereon. This acoustic matching layer 46 has a lower acoustic impedance than the inorganic piezoelectric layer 43b, and is configured by a silicon substrate that has a higher acoustic impedance than an organic piezoelectric layer 44b. Individual signal wiring 46a for each organic piezoelectric element 44 is formed on a surface opposite to the inorganic piezoelectric layer 43b. The structure of the individual signal wiring 46a in the example shown in FIG. 4 is same as that of the individual signal wiring 34a shown in FIG. 3.

The organic piezoelectric elements 44 are provided on the acoustic matching layer 46. In each of the organic piezoelectric elements 44, an individual electrode 44a formed for each element 44, the organic piezoelectric layer 44b made of PVDF, and a common (GND) electrode 44c are laminated in substantially a sound axis direction. In the organic piezoelectric element 44, the electrodes 44a, 44c are formed on front and rear surfaces of the sheet-like organic piezoelectric layer 44b. Subsequently, a flexible printed substrate 48 is connected to the acoustic matching layer 46 such that the individual signal wiring matches the other.

Such a configuration of each piezoelectric element in which the organic piezoelectric layer 44b capable of receiving a high-frequency signal of a harmonic bandwidth with a high degree of sensitivity is laminated on the inorganic piezoelectric layer 43b capable of high-power transmission can solve the problems involved in the complicated layout of the individual signal wiring 47, 46a. In the present embodiment, the individual signal wiring 47 of the inorganic piezoelectric layer 43b is formed via the backing layer 42, and the individual signal wiring 46a of the organic piezoelectric layer 44b is formed on the acoustic matching layer 46 between the piezoelectric layers 43b, 44b. However, when it is possible to form the individual signal wiring of the organic piezoelectric layer 44b on an acoustic matching layer on the subject side, the individual signal wiring of the inorganic piezoelectric layer 43b may be formed on the acoustic matching layer 46 between the piezoelectric layers 43b, 44b, to configure the array-type ultrasonic vibrator 41. Not only the PVDF but also polyvinylidine trifluoride copolymer (P(VDF-TrFE) or polyurea with an acoustic impedance of approximately 3 to 5 Mrayl can be used for forming the organic piezoelectric layer 44b.

In the configuration of the present embodiment, when laminating the inorganic piezoelectric layer and the organic piezoelectric layer, the acoustic matching layer having an acoustic impedance between the acoustic impedances of these piezoelectric layers is disposed between these piezoelectric layers, and the individual signal wiring for the organic piezoelectric elements are formed on this acoustic matching layer. With this configuration, the individual signal wiring can be easily laid out in the lamination-type ultrasonic vibrator, leading to a cost reduction.

Embodiment 3

Figure 6:
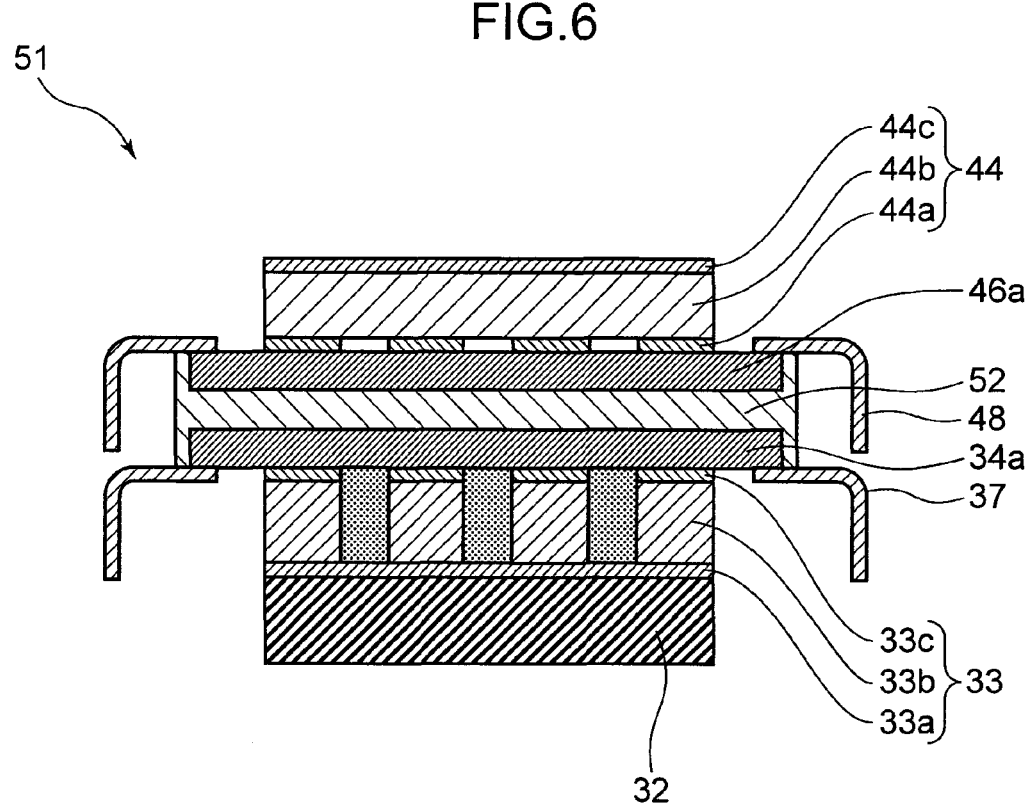
FIG. 6 is a vertical cross-sectional diagram showing a structural example of an array-type ultrasonic vibrator according to a third embodiment of the present invention.

FIG. 6 is a vertical cross-sectional diagram showing a structural example of an array-type ultrasonic vibrator 51 according to a third embodiment of the present invention. This array-type ultrasonic vibrator 51 is similar to the array-type ultrasonic vibrators 31, 41 described above. Therefore, the same reference numerals are used for indicating the corresponding parts, and the explanations thereof are omitted. In the array-type ultrasonic vibrator 51 of the present embodiment, an acoustic matching layer 52 is configured by a double-sided silicon substrate. The individual signal wiring 46a of the organic piezoelectric layer 44b and the individual signal wiring 34a of the inorganic piezoelectric layer 33b are formed, respectively, on front and rear surfaces of the acoustic matching layer 52. A pattern of the integrated circuit is also formed in the acoustic matching layer 52. Therefore, the backing layer 32 is not provided with the individual signal wiring 47, and the organic piezoelectric layer 44b on the subject side is also not provided with the individual signal wiring.

The thickness of the acoustic matching layer 52 is ¼ of a transmitted wavelength of the inorganic piezoelectric elements 33. Note in FIG. 6 that the acoustic matching layer 52 is formed as a double-sided substrate, but when the individual signal wiring 46a, 34a are formed only on one side of the acoustic matching layer 52, a substrate formed by pasting two pieces of substrates may be used. In this case, the thickness of the adhesive layer is made sufficiently thinner than the wavelength of the transmitted ultrasonic wave, so as not to have an impact on acoustic matching. Also, the thickness of the pasted two substrates including the adhesive layer is set at ¼ of the transmitted wavelength.

Figure 7:
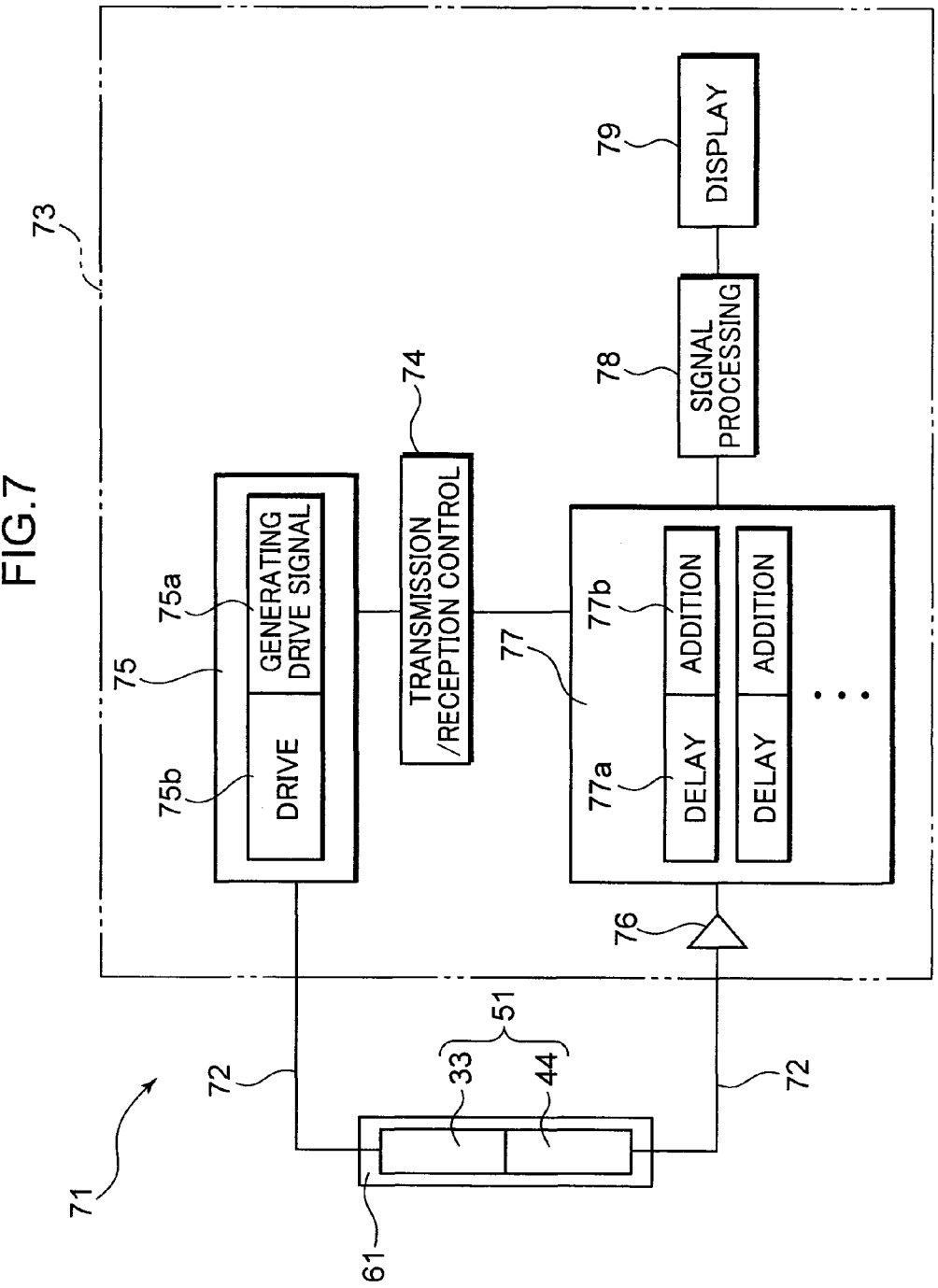
FIG. 7 is a block diagram showing a schematic configuration of an ultrasonic diagnostic apparatus in which an array-type ultrasonic vibrator is used as an ultrasonic probe.

The integrated circuit formed in the acoustic matching layer 52 is at least one of a drive circuit for driving each of the inorganic piezoelectric elements 33, a buffer circuit for amplifying a signal received by each of the organic piezoelectric elements 44, and a beam forming circuit for beamforming the amplified signal. FIG. 7 is a block diagram showing a schematic configuration of an ultrasonic diagnostic apparatus 71 in which the array-type ultrasonic vibrator 51 is used as an ultrasonic probe 61. The ultrasonic probe 61 is connected to an ultrasonic diagnostic apparatus main body 73 by a cable 72. As described hereinafter, a part of a function block provided in the ultrasonic diagnostic apparatus main body 73 is sometimes embedded in the array-type ultrasonic vibrator 51.

The ultrasonic diagnostic apparatus main body 73 generates a transmission pulse from a drive circuit 75 on the basis of control by a transmission/reception controller 74, and supplies the transmission pulse to each inorganic piezoelectric element 33. The drive circuit 75 functioning as a transmission beamformer causes a drive signal generating circuit 75a to generate, sequentially, pulses having a delay time adjusted for each row, in response to a transmission signal from the transmission/reception controller 74. The pulses are amplified by a drive element 75b and then supplied to the piezoelectric elements 33. As a result, a transmission beam focused on a focal point corresponding to a desired depth and desired scanning position is generated for the subject.

On the other hand, ultrasonic waves from the subject (reflected waves and harmonics) are received by the organic piezoelectric elements 44, and signals corresponding to the ultrasonic waves are subjected to impedance conversion by the buffer circuit 76 and then amplified if need be. Thereafter, the signals are input sequentially to a beam forming circuit 77 functioning as a receiving beamformer. The delay time is adjusted for each row by a delay circuit 77a, and the resultant signals are phased and added by an adding circuit 77b, to generate a reception beam corresponding to the transmission beam. The reception beam is input to a signal processing circuit 78 realized by a digital signal processor and the like, to create a tomographic image of the subject. The tomographic subject is then displayed by a display unit 79.

In this ultrasonic diagnostic apparatus 71, at least one of the drive circuit 75, the buffer circuit 76, and the beam forming circuit 77 is mounted in the integrated circuit that is formed in the acoustic matching layer 52 along with the individual signal wiring 34a, 46a, the acoustic matching layer 52 having the silicon substrates. Accordingly, the number of signal lines connected from and to the silicon substrates can be reduced significantly.

Especially by mounting the buffer circuit 76 and the beam forming circuit 77 in the integrated circuit of the silicon substrates of the acoustic matching layer 52, the number of signal lines can be reduced to one (or two including the GND) even if there are 32×32=1024 piezoelectric elements. When the reception piezoelectric elements 44 are organic, the permittivity thereof becomes small and the output impedance increases significantly, causing great transmission loss due to the wiring capacity. In order to minimize the transmission loss, the use of a method called "shield drive" is generally effective. However, this method needs to shield the individual signal lines, complicating the wiring structures. In fact, the number of lines becomes twice as high. For this reason, forming the buffer circuit 76 as the integrated circuit of the acoustic matching layer 52 eliminates the need of a complicated shield structure, due to the presence of the reception buffer circuit in the vicinity of the individual piezoelectric elements 44. This is effective because the transmission loss caused due to the wiring capacity can be reduced and only the same number of signal lines as the elements is needed.

Increasing the number of piezoelectric elements generates a large difference in delay time between the elements close to the target (focal point) and the elements far from the target. The plurality of elements near the target may be combined to form sub-arrays, and the delay time may be adjusted for each sub-array to perform sub-array beam forming. Then, the delay time may be adjusted for each sub-array on the subsequent level to perform main beam forming, so as to configure the beam forming circuit 77. In this case, the delay circuit 77a adjusts the delay time in each sub-array, and the size of the delay circuit 77a can be reduced. However, the signal wiring consists of multiples of the number of sub-arrays; when there are sixteen sub-arrays, the number of signal lines becomes 1024/16=64.

In the present embodiment, the plate-like body configuring the acoustic matching layer 52 is configured by the silicon substrates, and the individual signal lines and the pattern of the integrated circuit are formed on the silicon substrates. Therefore, the number of signal lines connected from and to the silicon substrates can be reduced significantly.

Embodiment 4

Figure 8:
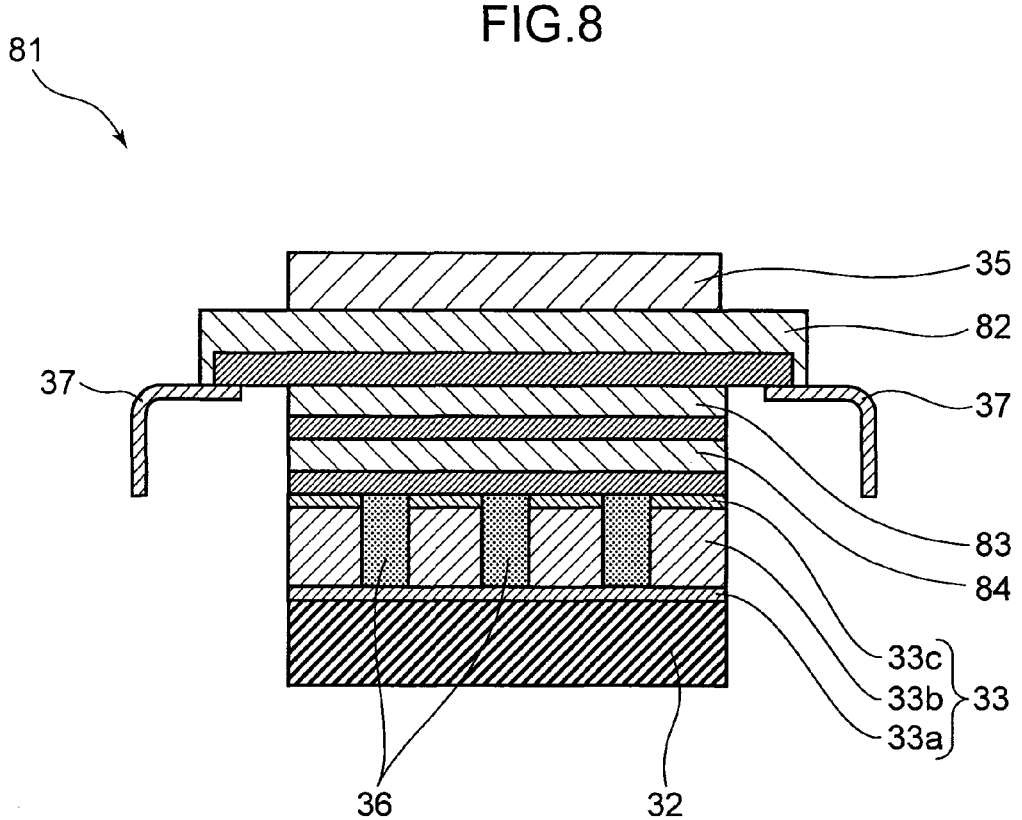
FIG. 8 is a vertical cross-sectional diagram showing a structural example of an array-type ultrasonic vibrator according to a fourth embodiment of the present invention.
Figure 9:
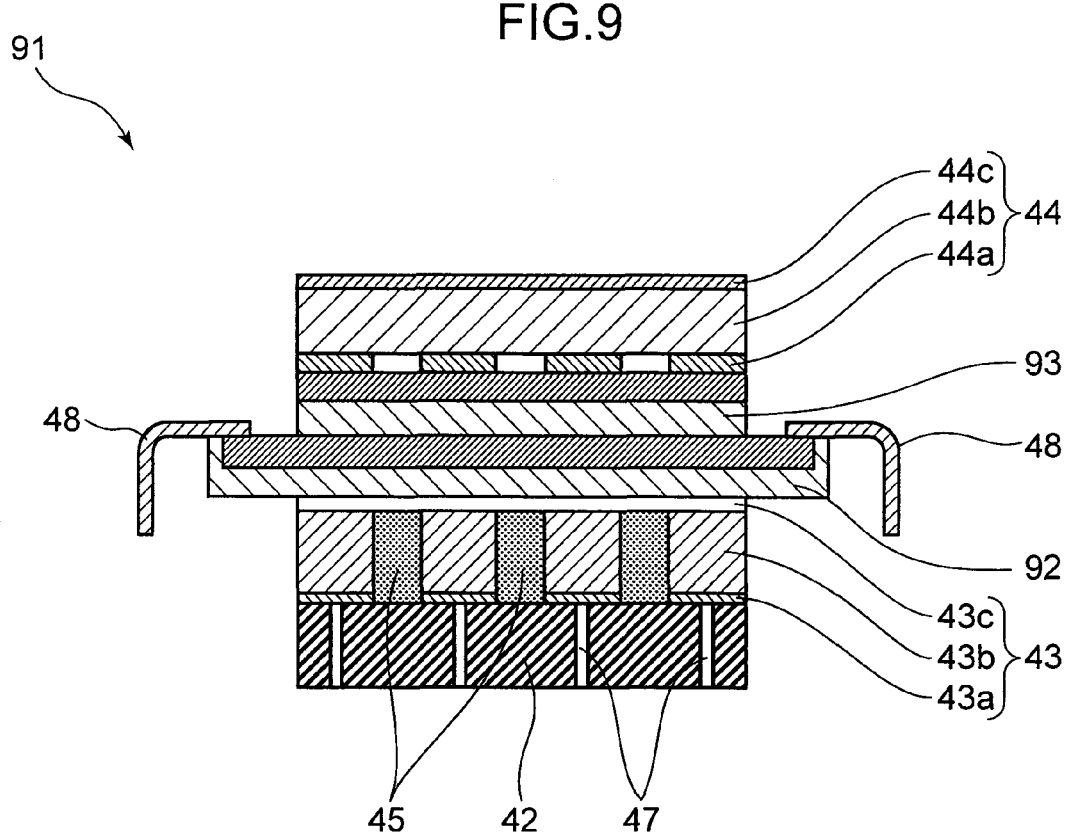
FIG. 9 is a vertical cross-sectional diagram showing a structural example of another array-type ultrasonic vibrator according to the fourth embodiment of the present invention.
Figure 10:
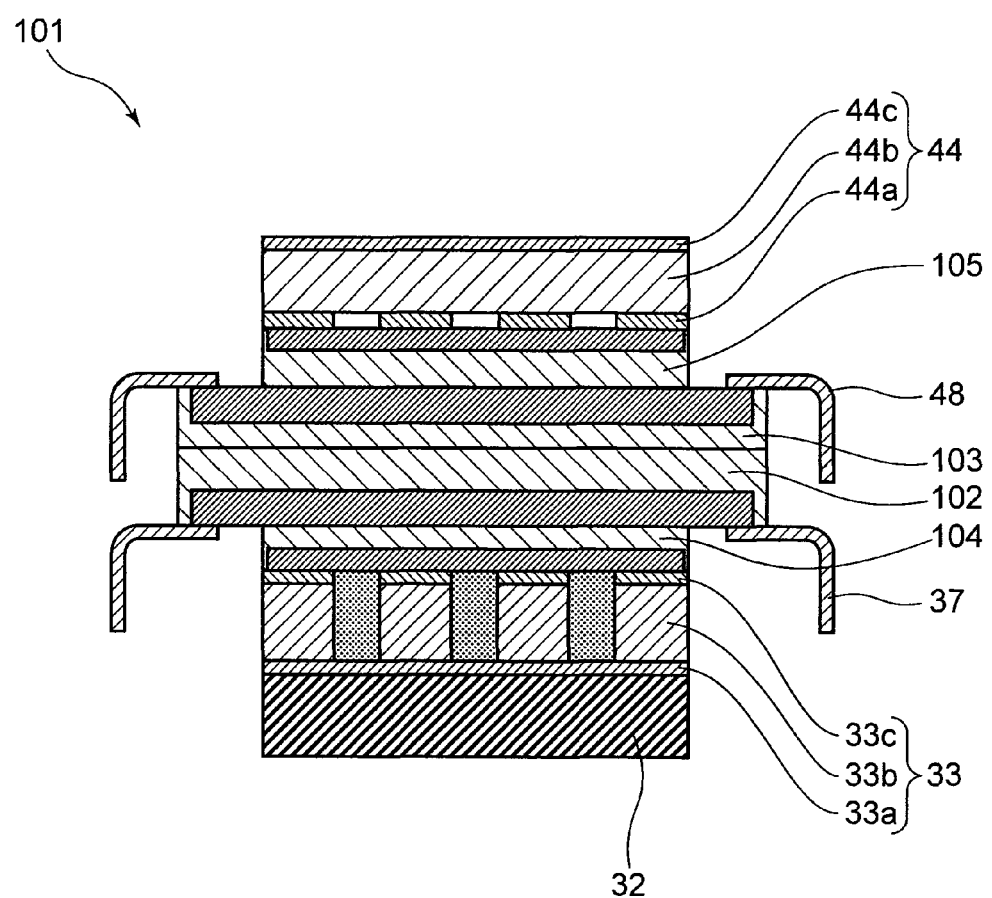
FIG. 10 is a vertical cross-sectional diagram showing a structural example of yet another array-type ultrasonic vibrator according to the fourth embodiment of the present invention.

FIGS. 8 to 10 are vertical cross-sectional diagrams showing structural examples of array-type ultrasonic vibrators 81, 91, 101 according to a fourth embodiment of the present invention. First, the array-type ultrasonic vibrator 81 shown in FIG. 8 is similar to the array-type ultrasonic vibrator 31 described above. Therefore, the same reference numerals are used for indicating the corresponding parts, and the explanations thereof are omitted. In the array-type ultrasonic vibrator 81 shown in FIG. 8, in place of the acoustic matching layer 34, which is a single-layer silicon substrate, a multilayer silicon substrate of a plurality of acoustic matching layers 82 to 84 laminated within a thickness of ¼ of the transmitted ultrasonic wave and having the pattern of the integrated circuit formed in at least one of the plurality of acoustic matching layers (layers 82 to 84 in FIG. 8) is provided.

According to this configuration, the integrated circuit can be divided and mounted when the elements cannot be integrated due to an integration degree or when the elements cannot be integrated on a single substrate due to different processes performed. For example, the abovementioned buffer circuit 76 is mounted as a transmission/reception switching circuit in the uppermost acoustic matching layer 82, the beam forming circuit 77 is then mounted in the next acoustic matching layer 83, and the drive circuit 75 is mounted in the lowermost acoustic matching layer 84. The acoustic matching layers 82 to 84 are connected by through electrodes, wherein the flexible printed substrate 37 is connected to the largest acoustic matching layer 82, and the integrated circuits of the acoustic matching layers 83, 84 are connected to the outside via the acoustic matching layer 82. In this manner, a lot of circuits related to the array-type ultrasonic vibrator can be embedded in the array-type ultrasonic vibrator.

The array-type ultrasonic vibrator 91 shown in FIG. 9 is similar to the array-type ultrasonic vibrator 41 described above. Therefore, the same reference numerals are used for indicating the corresponding parts, and the explanations thereof are omitted. In the array-type ultrasonic vibrator 91 shown in FIG. 9, a plurality of acoustic matching layers are laminated within a thickness of ¼ of the transmitted ultrasonic wave, in place of the acoustic matching layer 46, which is a single-layer silicon substrate. Acoustic matching layers 92, 93, each of which is a multilayer silicon substrate having the pattern of the integrated circuit formed therein, are provided in the plurality of acoustic matching layers respectively. For example, the buffer circuit 76 is mounted in the upper acoustic matching layer 93, and the beam forming circuit 77 is mounted in the lower acoustic matching layer 92.

The array-type ultrasonic vibrator 101 shown in FIG. 10 is similar to the array-type ultrasonic vibrator 51 described above. Therefore, the same reference numerals are used for indicating the corresponding parts, and the explanations thereof are omitted. In the array-type ultrasonic vibrator 101 shown in FIG. 10, a plurality of acoustic matching layers are laminated within a thickness of ¼ of the transmitted ultrasonic wave, in place of the acoustic matching layer 52. Acoustic matching layers 102 to 105, each of which is a multilayer silicon substrate having the pattern of the integrated circuit formed therein, are provided in the plurality of acoustic matching layers respectively. A layer obtained by pasting the acoustic matching layers 102, 103 together serves as the double-sided acoustic matching layer 52, and the multilayer acoustic matching layers 104, 105 are laminated to the acoustic matching layers 102, 103, respectively. A transmission circuit is mounted in the acoustic matching layers 102, 104 on the transmission inorganic piezoelectric elements 33 side, while a reception circuit is mounted in the acoustic matching layers 103, 105 on the reception organic piezoelectric elements 44 side.

According to the configuration of the present embodiment, each silicon substrate is formed as a multilayer substrate that does not have an impact on transmission/reception and has the plurality of acoustic matching layers formed within a thickness of ¼ of the transmitted ultrasonic wave. At least one of these layers has the pattern of the integrated circuit such as the drive circuit, buffer circuit and beam forming circuit formed therein. A lot of circuits related to the array-type ultrasonic vibrator can therefore be embedded in the array-type piezoelectric elements.

Embodiment 5

Figure 11:
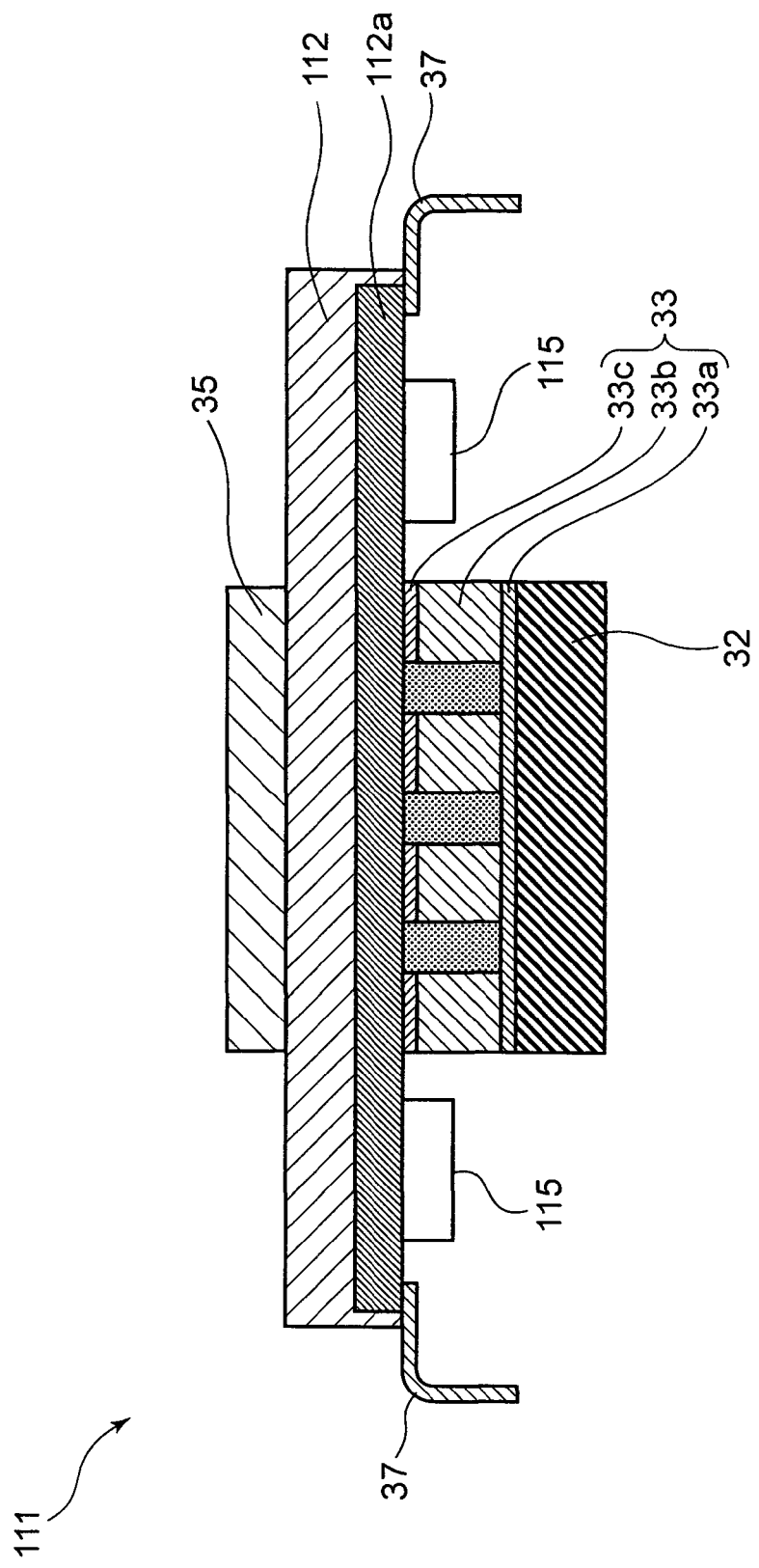
FIG. 11 is a vertical cross-sectional diagram showing a structural example of an array-type ultrasonic vibrator according to a fifth embodiment of the present invention.
Figure 12:
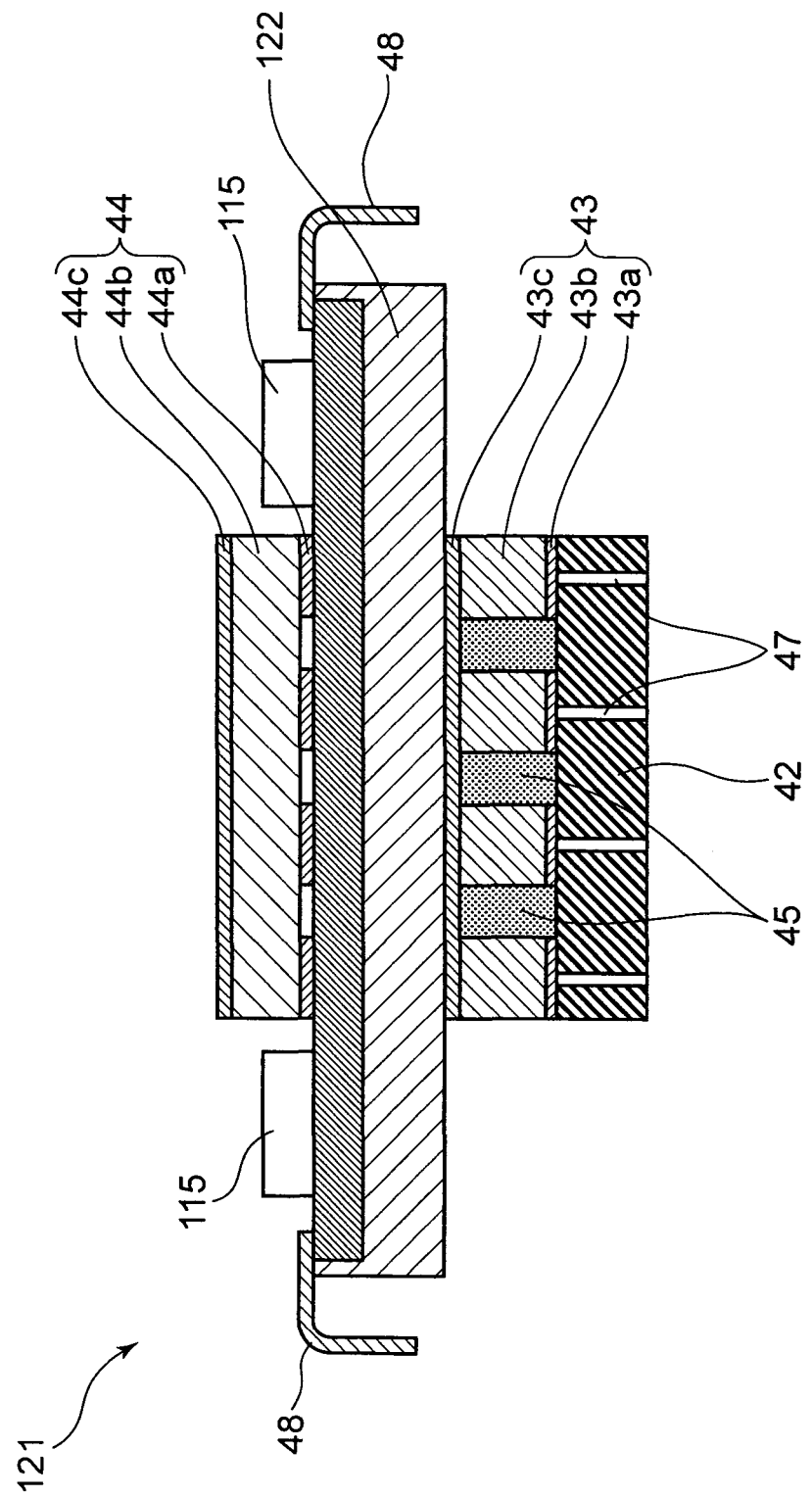
FIG. 12 is a vertical cross-sectional diagram showing a structural example of another array-type ultrasonic vibrator according to the fifth embodiment of the present invention.
Figure 13:
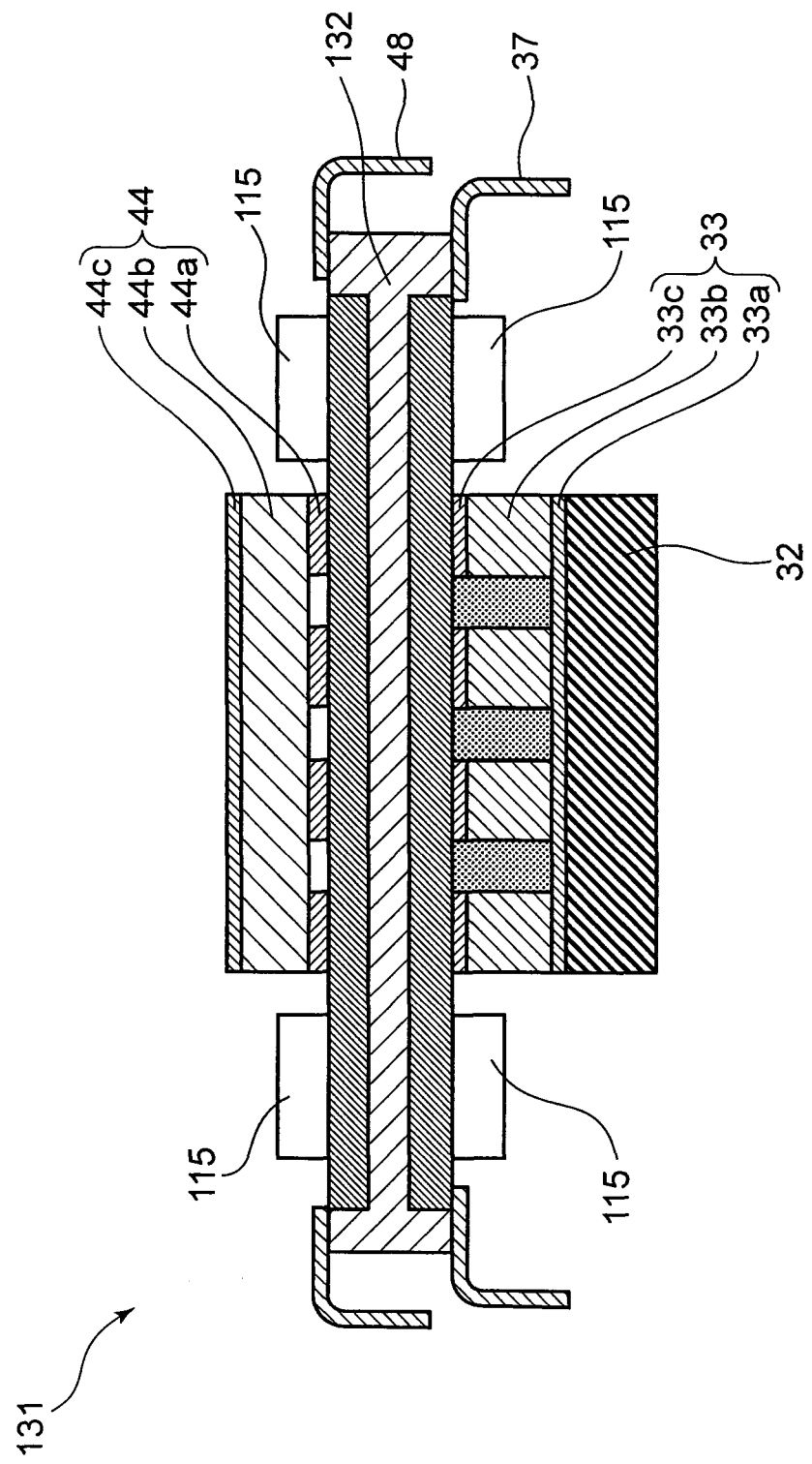
FIG. 13 is a vertical cross-sectional diagram showing a structural example of yet another array-type ultrasonic vibrator according to the fifth embodiment of the present invention.

FIGS. 11 to 13 are vertical cross-sectional diagrams showing structural examples of array-type ultrasonic vibrators 111, 121, 131 according to a fifth embodiment of the present invention. First, the array-type ultrasonic vibrator 111 shown in FIG. 11 is similar to the array-type ultrasonic vibrator 31 described above. Therefore, the same reference numerals are used for indicating the corresponding parts, and the explanations thereof are omitted. The array-type ultrasonic vibrator 111 shown in FIG. 11 is configured by the same silicon substrate, wherein an acoustic matching layer 112 wider than the array-type piezoelectric elements 33 is used in place of the acoustic matching layer 34, and integrated circuit chips 115 are placed on the projecting parts of the acoustic matching layer 112. In other words, individual signal wiring 112a is simply formed in the silicon substrate, and the integrated circuits are formed separately as the chips 115. This configuration can significantly reduce the number of signal lines connected from and to the silicon substrate, and a large circuit having all of the drive circuit 75, the buffer circuit 76 and the beam forming circuit 77 can be mounted on the silicon substrate. In addition, each of the chips 115 can be created using an appropriate process or placed on different layers, depending on delivery destinations.

The array-type ultrasonic vibrator 121 shown in FIG. 12 is similar to the array-type ultrasonic vibrator 41 described above. In this array-type ultrasonic vibrator 121, a wide acoustic matching layer 122 is used in place of the acoustic matching layer 46, and the integrated circuit chips 115 are placed on the projecting parts of the acoustic matching layer 122. The array-type ultrasonic vibrator 131 shown in FIG. 13 is similar to the array-type ultrasonic vibrator 51 described above. In this array-type ultrasonic vibrator 131, a wide acoustic matching layer 132 is used in place of the acoustic matching layer 52, and the integrated circuit chips 115 are placed on the projecting parts of the acoustic matching layer 132.

In each of the array-type ultrasonic vibrators of the present embodiment, the silicon substrate is made wider than the area occupied by the array-type piezoelectric elements, and each integrated circuit chip is placed on an area other than the area of the silicon substrate.

The plate-like body configuring each acoustic matching layer is configured by the silicon substrate, and the silicon substrate is made wider than the array-type piezoelectric elements. Moreover, the individual signal wiring is formed on the silicon substrate, and the integrated circuit chips are placed on the sections projecting from the piezoelectric elements. Therefore, the number of signal lines connected from and to the silicon substrate can be reduced significantly. In addition, a large circuit having all of the drive circuit, the buffer circuit and the beam forming circuit can be mounted on the silicon substrate.

The present specification discloses a variety of aspects of technologies as above. The following describes a summary of the main technologies.

An array-type ultrasonic vibrator of a first aspect has a backing layer, a plurality of piezoelectric elements arrayed on the backing layer, an acoustic matching layer that is provided on the plurality of piezoelectric elements and configured by a plate-like body made of a material having a lower acoustic impedance than the plurality of piezoelectric elements, and signal wiring formed on the plate-like body of the acoustic matching layer. It is preferred that the plurality of piezoelectric elements be arrayed two-dimensionally. It is also preferred that the signal wiring be connected to the plurality of piezoelectric elements individually.

According to the array-type ultrasonic vibrator having such configuration, the signal wiring can be formed on the backing layer, or the signal wiring can be formed easily without using additional components. This leads to a cost reduction and high definition (increase in the number of elements).

According to a second aspect, in the array-type ultrasonic vibrator described above, the plurality of piezoelectric elements are inorganic piezoelectric elements. The array-type ultrasonic vibrator has a plurality of organic piezoelectric elements arrayed on the acoustic matching layer, and the signal wiring is connected to the plurality of organic piezoelectric elements individually.

According to this configuration, the array-type ultrasonic vibrator is suitably used in a piezoelectric element having a laminated structure in which it is difficult to lay out individual signal wiring.

According to a third aspect, in the array-type ultrasonic vibrators described above, the plate-like body is a silicon substrate.

According to this configuration, not only is it possible to form the individual signal wiring easily, but also fine individual signal wiring can be obtained. Therefore, these array-type ultrasonic vibrators are suitable for accomplishing high definition (increase in the number of elements).

According to a fourth aspect, in the array-type ultrasonic vibrator described above, an integrated circuit is formed on the silicon substrate.

According to this configuration, the number of signal lines connected from and to the silicon substrate can be reduced significantly.

According to a fifth aspect, in the array-type ultrasonic vibrator described above, the integrated circuit is at least one of a drive circuit for driving each of the piezoelectric elements, a buffer circuit for amplifying a signal received by each of the piezoelectric elements, and a beam forming circuit for beamforming the amplified signal.

According to this configuration, the number of signal lines connected to the silicon substrate can be significantly reduced by placing the integrated circuit.

According to a sixth aspect, in the array-type ultrasonic vibrators described above, the silicon substrate is laminated in plurality to form a multilayer substrate, with at least one of the silicon substrates being configured to have the integrated circuit formed thereon. It is preferred that the plurality of silicon substrates be laminated within a thickness of ¼ of a transmitted ultrasonic wave so as not to have an impact on transmission/reception.

According to this configuration, a lot of circuits related to the array-type piezoelectric elements can be embedded in the array-type piezoelectric elements.

According to a seventh aspect, in these array-type ultrasonic vibrators described above, the silicon substrate is formed to be wider than an area occupied by the plurality of piezoelectric elements, and an integrated circuit chip is disposed in an area other than the area of the silicon substrate.

According to this configuration, the number of signal lines connected from and to the silicon substrate can be reduced significantly, and a large circuit with all of the drive circuit, the buffer circuit and the beam forming circuit can be mounted on the silicon substrate.

This application is based on Japanese Patent Application No. 2008-268344 filed on Oct. 17, 2008, the contents of which are hereby incorporated.

The present invention was described above using the embodiments and the diagrams. However, it should be recognized that a person skilled in the art can easily change and/or improve the embodiments. Therefore, as long the changes or improvements made by the person skilled in the art do not depart from the scope of the claims described in the present specification, such changes or improvements are interpreted as being included in the scope of the claims.

INDUSTRIAL APPLICABILITY

The present invention can provide an array-type ultrasonic vibrator.

The invention claimed is:

1. An array-type ultrasonic vibrator, comprising:
a backing layer;
a plurality of piezoelectric elements arrayed on the backing layer;
an acoustic matching layer that is provided on the plurality of piezoelectric elements and configured by a plate-like body made of a material having a lower acoustic impedance than the plurality of piezoelectric elements; and
signal wiring formed on the plate-like body of the acoustic matching layer.

2. The array-type ultrasonic vibrator according to claim 1, wherein the plurality of piezoelectric elements are arrayed two-dimensionally.

3. The array-type ultrasonic vibrator according to claim 1, wherein the signal wiring has a plurality of branches that are each connected to one of the plurality of piezoelectric elements individually.

4. The array-type ultrasonic vibrator according to claim 1, wherein:
the plurality of piezoelectric elements are inorganic piezoelectric elements;
the array-type ultrasonic vibrator has a plurality of organic piezoelectric elements arrayed on the acoustic matching layer; and
the signal wiring is connected to the plurality of organic piezoelectric elements individually.

5. The array-type ultrasonic vibrator according to claim 1, wherein the plate-like body is a silicon substrate.

6. The array-type ultrasonic vibrator according to claim 5, wherein an integrated circuit is formed on the silicon substrate.

7. The array-type ultrasonic vibrator according to claim 6, wherein the integrated circuit is at least one of a drive circuit for driving each of the piezoelectric elements, a buffer circuit for amplifying a signal received by each of the piezoelectric elements, and a beam forming circuit for beamforming the amplified signal.

8. The array-type ultrasonic vibrator according to claim 6, wherein the silicon substrate is laminated in plurality to form a multilayer substrate, with at least one of the silicon substrates being configured to have the integrated circuit formed thereon.

9. The array-type ultrasonic vibrator according to claim 5, wherein the silicon substrate is formed to be wider than an area occupied by the plurality of piezoelectric elements, and an integrated circuit chip is disposed in an area other than the area of the silicon substrate.

10. The array-type ultrasonic vibrator according to claim 1, wherein the plurality of piezoelectric elements are spaced from each other on the backing layer by gaps between the piezoelectric elements.

11. The array-type ultrasonic vibrator according to claim 1, wherein the plurality of piezoelectric elements are directly on a common ground electrode.

12. The array-type ultrasonic vibrator according to claim 1, further comprising a flexible printed substrate having wiring that is connected to the individual signal wiring on the plate-like body of the acoustic matching layer.

* * * * *